United States Patent
Sief et al.

(10) Patent No.: US 9,073,768 B2
(45) Date of Patent: Jul. 7, 2015

(54) IN-LINE UV-GERMICIDAL DEVICE FOR FLUID MEDIA

(75) Inventors: Rolf Sief, Kreuzlingen (CH); Friedhelm Kruger, Lemgo (DE)

(73) Assignee: Xylem IP Holdings LLC, White Plains, NY (US)

( * ) Notice: Subject to any disclaimer, the term of this patent is extended or adjusted under 35 U.S.C. 154(b) by 918 days.

(21) Appl. No.: 12/596,039

(22) PCT Filed: Mar. 6, 2008

(86) PCT No.: PCT/EP2008/001794
§ 371 (c)(1),
(2), (4) Date: Oct. 29, 2010

(87) PCT Pub. No.: WO2008/128600
PCT Pub. Date: Oct. 30, 2008

(65) Prior Publication Data
US 2011/0076188 A1    Mar. 31, 2011

(30) Foreign Application Priority Data
Apr. 18, 2007  (DE) .......................... 10 2007 018 670

(51) Int. Cl.
C02F 1/32 (2006.01)
A61L 2/10 (2006.01)
C02F 103/00 (2006.01)

(52) U.S. Cl.
CPC . *C02F 1/325* (2013.01); *A61L 2/10* (2013.01); *C02F 2103/008* (2013.01); *C02F 2201/322* (2013.01); *C02F 2201/3225* (2013.01); *C02F 2201/3227* (2013.01); *C02F 2201/328* (2013.01)

(58) Field of Classification Search
CPC ......... A61L 2/10; A61L 2202/11; C02F 1/32; C02F 1/325; C02F 2201/322; C02F 2201/3225; C02F 201/3227; C02F 2201/328
USPC .............................................. 422/24, 186.3, 6
See application file for complete search history.

(56) References Cited

U.S. PATENT DOCUMENTS

| 5,200,156 A | 4/1993 | Wedekamp |
| 5,779,912 A | 7/1998 | Gonzalez-Martin |

(Continued)

FOREIGN PATENT DOCUMENTS

| DE | 42 10 509 A1 | 10/1993 |
| EP | 1837309 A1 | 9/2007 |

(Continued)

OTHER PUBLICATIONS

Machine Translation of DE4210509, retrieved from esp@cenet on Sep. 19, 2012.*
International Search Report of PCT/EP2009/003914, mailed Sep. 28, 2009.

*Primary Examiner* — Timothy Cleveland
(74) *Attorney, Agent, or Firm* — RatnerPrestia

(57) ABSTRACT

The invention relates to a device for the sterilization of ballast water on ships by means of UV radiation, with a pump line by means of which ballast water can be taken up and discharged, wherein the pump line is passed through by a number of UV-transparent sheath pipes arranged one behind another in the direction of the pump line and in which UV radiators are arranged for the emission of UV radiation into the pump line and sheath pipes arranged one behind another in the circumferential direction of the pump line are offset by an angle α in relation to one another.

14 Claims, 3 Drawing Sheets

(56) References Cited

U.S. PATENT DOCUMENTS

| | | |
|---|---|---|
| 7,592,607 B2 | 9/2009 | Sief et al. |
| 7,683,354 B2 | 3/2010 | Girodet et al. |
| 2004/0055966 A1 | 3/2004 | Nguyen et al. |
| 2004/0069954 A1 | 4/2004 | Traubenberg et al. |
| 2007/0290144 A1 | 12/2007 | Sief |
| 2008/0105606 A1 | 5/2008 | Girodet et al. |

FOREIGN PATENT DOCUMENTS

| | | |
|---|---|---|
| FR | 2 881 130 | 7/2006 |
| WO | WO 02/079095 A1 | 10/2002 |
| WO | WO03/091167 A1 | 11/2003 |
| WO | WO2008/059503 A1 | 5/2008 |
| WO | WO2008/128600 A2 | 10/2008 |

* cited by examiner

IN-LINE UV-GERMICIDAL DEVICE FOR FLUID MEDIA

CROSS REFERENCE TO RELATED APPLICATIONS

This application is the U.S. national phase application of PCT International Application No. PCT/EP2008/001794, filed Mar. 6, 2008, which claims priority to DE 10 2007 018 670.6, filed Apr. 18, 2007, and PCT International Application No. PCT/EP2008/000581, filed Jan. 25, 2008, the contents of such applications being incorporated by reference herein.

FIELD OF THE INVENTION

The present invention relates to a UV-germicidal device for fluid media, preferably with low transmission and high required UV intensity, in particular for ballast water in shipping.

BACKGROUND OF THE INVENTION

Ballast water is taken on by ships in order to attain a more stable position in the water with a small cargo. For this purpose ballast tanks are provided, into which, at the departure port before a journey with small cargo, seawater is pumped directly from the harbour. With this taking on of ballast water, organisms are also taken on, which are conveyed on the voyage in the ballast tank. The water taken on undergoes only coarse filtering.

In the destination port the ballast water is then discharged in order to re-establish the full loading capacity of the vessel once more. The ballast water is then pumped out of the tanks into the surrounding water when outside or in the destination port. Because the departure port and the destination port form different ecosystems, especially with overseas voyages, the risk should be avoided of the organisms taken up with the ballast water being discharged into the foreign ecosystem. To achieve this, the ballast water is disinfected when taken on and/or when being discharged.

According to the prior art, the disinfection device is incorporated in the pump line, specifically with disinfection by UV radiation sources in the form of radiation units aligned transversely to the direction of flow. The radiation units are in this situation either arranged one behind another in one plane in the direction of flow, or in two planes, likewise one behind another in the direction of flow but arranged offset against the mid-axis of the pipe at a distance from one another. A further variant is known in which numerous UV radiators are arranged in two planes parallel to the mid-axis of the pipe, but are aligned at an angle to the direction of flow. In this way a greater radiation length can be used with a given diameter of the pipe.

SUMMARY OF THE INVENTION

The radiator arrangements mentioned have the fact in common that, next to the planes in which the radiator groups are arranged, flow paths form with a low intensity of UV radiation. In these flow paths, which in the variant first referred to are located above and below the radiator plane and in the second and third known variant are also located between the radiator planes, the probability of survival of the organisms contained in the water is too great. This applies in particular if the transmission of the ballast water for UV radiation is restricted.

The desired disinfection performances can only be achieved with these devices with high usage of radiation power. To achieve this, a large number of high-performance radiators are required, which incur correspondingly high costs.

The present invention provides a UV disinfection device for ballast water which, when arranged in a pump line, produces a substantially better disinfection performance with a comparable number of radiators and a similar energy consumption.

In one embodiment of the present invention, UV radiators are arranged behind one another in the flow direction such that they are offset against one another at an angle in relation to the radial direction. In this manner, the probability is reduced of the micro-organisms or other substances contained in the medium to be disinfected passing through the device on a flow path which does not have an adequate UV intensity.

Further embodiments of the invention are presented in the dependent claims.

In one embodiment, a good effect is shown if the angle α amounts to 15° to 45°, and preferably 30°. Depending on the embodiment, the angle α can, for example, be selected as dependent on the pipe diameter.

In another embodiment, radiators with greater discharge lengths can be used if the sheath pipe is inclined against the radial direction of the pump line by an angle β of 30° to 70°.

A broad irradiation of all possible flow paths is achieved if at least two groups of sheath pipes are provided, of which one sheath pipe in each case is arranged in relation to the mid-axis of the pump line next to a sheath pipe of the other group and wherein the groups in each case form a separate screw-shaped row. For a particularly high throughput and/or media with particularly low UV transmission, three or more radiators can be arranged next to one another in a radial plane. In this situation the areas of the pump line close to the wall are also reached if the sheath pipes are arranged at a distance from the mid-axis.

In a further embodiment, the groups may have different distance intervals from the mid-axis, namely a first group has a large distance interval and a second group a small distance interval. In addition, the first group can be aligned at a large angle β of 50° to 70° and the second group at a smaller angle β of 30° to 49° to the radial direction, such that both groups can be equipped with the same radiators.

In yet another embodiment, the larger distance interval can amount to more than 60% of the radius of the pump line and the smaller distance interval less than 40% of the radius of the pump line. In particular, the one distance interval can be 75% of the radius of the pump line and the second distance interval 20% of the radius of the pump line. The formation of flow paths with undesirably high flow speeds or low intensity can be avoided if the axial distance interval is varied within a group, for example if the first group has on average a distance interval of 60% of the radius but fluctuates by +/−10%, while the second group has on average a distance interval of 20% of the radius, which likewise varies by +/−10% of the radius.

In at least one embodiment of the present invention, a particularly good ratio is achieved between the number of radiators used and the effect achieved if each of the groups of sheath pipes comprises a total of 12 sheath pipes.

BRIEF DESCRIPTION OF THE DRAWINGS

The present invention is described in greater detail hereinafter on the basis of the drawings and two embodiments. The drawings show.

DETAILED DESCRIPTION OF THE INVENTION

To provide an explanation of the technical preconditions, the use of UV disinfection systems for the disinfection of ballast water should first be described. Disinfection in this situation means a reduction in the live micro-organisms contained in it.

The ballast water is taken up through a pump line and stored in tanks. At the destination, the ballast water is again discharged through the pump line. A disinfection procedure in which the whole of the water must be subjected to a specific UV dosage can therefore only take place in the pump line itself, since not all areas of the tank can be irradiated. Disinfection in the tank during the voyage with UV radiation therefore cannot be carried out without additional installed elements. Chemical disinfection should not be carried out because of possible residues of the disinfection media in the ballast water.

In addition, because the take-up and discharge of ballast water should be carried out as rapidly as possible in order to make voyage and demurrage times as short as possible, a high flow rate is to be expected in the pump line. In order to subject the water to a minimum UV dosage, a high UV intensity is therefore required at the site of the irradiation, i.e. in the pump line. This intensity is achieved by a number of high-performance UV radiators. The radiators themselves are arranged in sheath pipes. These sheath pipes are made of quartz and run through the pump line in such a way that they are inserted in a sealing manner into the wall. The radiators are then in turn inserted into the sheath pipes, such that they do not come in contact with the ballast water but can emit their radiation effect into the ballast water through the sheath pipe.

Figure 1:
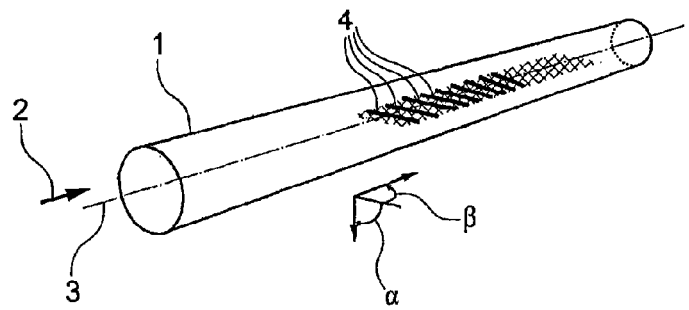
FIG. 1: A disinfection device according to the prior art, with a single-row radiator arrangement, which has radiators aligned at an angle of 90° to the direction of flow.
Figure 2:
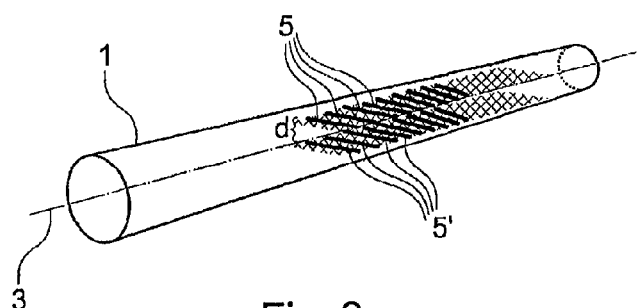
FIG. 2: A disinfection device with two rows of radiators arranged in the radial direction at a distance from the axis, which likewise have an angle of 90° to the direction of flow.
Figure 3:
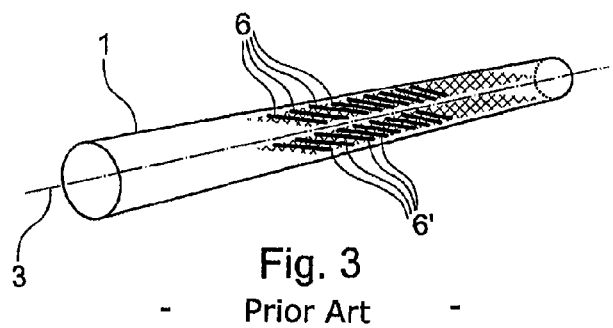
FIG. 3: A disinfection system with two rows of radiators at a radial distance interval from one another, wherein the radiators have an angle of about 50° to the direction of flow of the medium.

In the first instance, the prior art may be explained on the basis of FIGS. 1-3. FIG. 1 shows a pump line 1 with an essentially circular cross-section. The direction of flow runs in the longitudinal direction of the pump line 1, which is indicated by the flow arrow 2. An axis of symmetry 3 symbolises the mid-axis of the pump line 1 and represents the rotational symmetry of the arrangement. It is possible to define two angles, namely one angle α, which is measured from a horizontally aligned radius in the circumferential direction and in the clockwise direction, and a second angle β, which is measured from a radius outwards in the direction of the axis of symmetry 3.

Located in the interior of the pump pipe 1 are a number of UV radiators which are aligned transverse to the direction of flow 2. In FIG. 1 they are represented as horizontal, i.e. they lie in one plane in relation to the mid-axis 3. The radiators 4 are arranged in the area of the greatest diameter of the pump line 1. In the sense of the angle definition explained above, the angle α measures 0° and the angle β likewise 0°. The individual radiators 4 lie precisely transverse to the mid-axis 3 and are penetrated by it.

The prior art embodiment according to FIG. 1 results in practice in flow paths being formed above and below the radiator 4, in which the UV dosage is relatively low, such that an effective disinfection can only be achieved with very high output from the radiators 4.

FIG. 2 shows another prior art, in which radiators 5 are arranged in a plane above the axis of symmetry 3, while a second set of radiators 5' is arranged below the axis of symmetry 3. The two groups of radiators 5 and 5' have the same distance interval from the axis of symmetry 3. The radiators are arranged horizontally and parallel to a diameter of the pump line 1. The angles α and β are likewise equal to 0°. A distance interval d between the mid-axis 3 and the radiator units 5 and 5' amounts to some 50% of the radius of the pump line 1. With this embodiment too, flow paths form which receive a relatively low UV dose, in particular with ballast water with low transmission.

Finally, FIG. 3 shows a further prior art. With this embodiment, UV radiators 6 and 6' are arranged, as in FIG. 2, in two planes parallel to the mid-axis of the pump line 1. In this case, the individual radiators 6 and 6', as a departure from the embodiments in FIG. 1 and FIG. 2, are inclined against the radius of the pump line 1. The angle β amounts to about 40°. The distance interval d corresponds to that in FIG. 2. The angle α is 0°.

With this configuration too, flow paths occur. Although, because of the high flow rate, the flow in the pump line 1 is turbulent in all cases, no complete intermixing of the pumped medium takes place in the transverse direction of the pump line. Rather, although individual particles in the pumped medium move in the transverse direction to the conveying direction 2, these particles remain on average on a path parallel to the mid-axis 3.

The present invention provides a radiator arrangement which allows every possible flow path to impinge on a UV radiator at least once in the course of the pump line.

Figure 4:
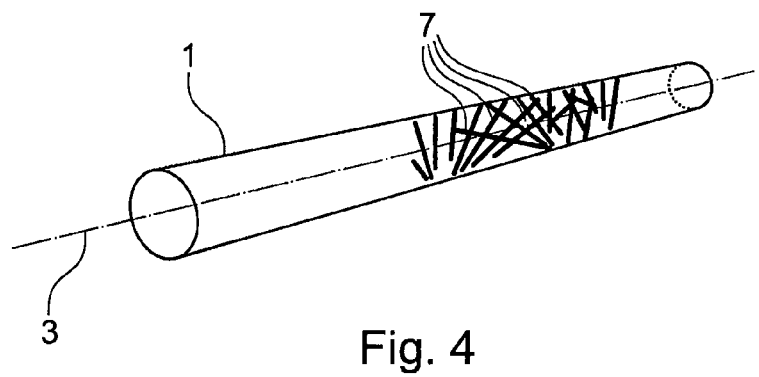
FIG. 4: A disinfection device according to an embodiment of the invention with a single row of radiators arranged in screw-shaped.

An embodiment of this invention is shown in the first instance in a representation in FIG. 4 corresponding to FIGS. 1-3. FIG. 4 shows the pump line 1 with a number of radiators 7, which in each case are offset to one another by an angle α. The angle α in this embodiment is about 30°. With this embodiment, the distance interval d for two radiators arranged next to one another is the same.

Figure 5:
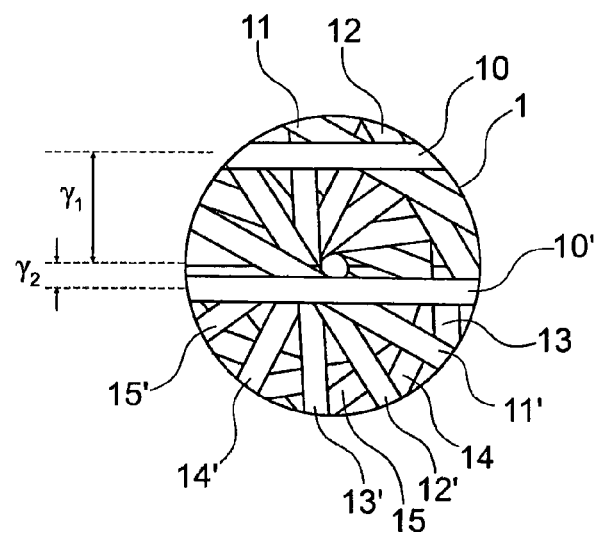
FIG. 5: A disinfection device similar to the embodiment of the invention shown in FIG. 4 with two rows located radially at a distance from one another, which are in each case arranged in screw-shaped.

FIG. 5 shows another embodiment, this time in a front view in the direction of the mid-axis 3 of the pump line 1. The representation shows a plurality of sheath pipes, which are numbered sequentially from front to back. Lying in the first plane are two sheath pipes 10 and 10'. The second plane located behind this is comprised of two sheath pipes 11 and 11'; the third plane of the sheath pipes 12 and 12'; and so on. The term "plane" in this connection is not to be understood strictly as a radial plane, but rather as the area in which two radiators lie next to one another in relation to the direction of flow of the pumped medium.

It can be seen that the sheath pipes 10, 11, 12, 13 have a distance interval r1 from the mid-axis 3, which amounts to about 75% of the radius of the pump line 1. The distance interval of the sheath pipes 10' 11', 12', 13' from the mid-axis 3 of the pump line 1 amounts to about 18% of the radius of the pump line 1.

While with the embodiment according to FIG. 4, the distance interval in each case between two radiators lying radially next to one another at the mid-axis 3 is the same, in FIG. 5 an embodiment is shown in which the distance interval between the two radiators lying next to one another is different. This embodiment is therefore preferred.

Seen in the direction of flow of the fluid to be disinfected, the arrangement according to FIG. 5 shows a type of double helix or super helix.

With the embodiment according to FIG. 5, the chord length available of the sheath pipes 10, 11, 12, 13 is shorter than that of the sheath pipes 10', 11', 12' 13'. This is compensated for by different angles β to the longitudinal axis 3 of the pump pipe 1, as can be seen from FIG. 6.

Figure 6:
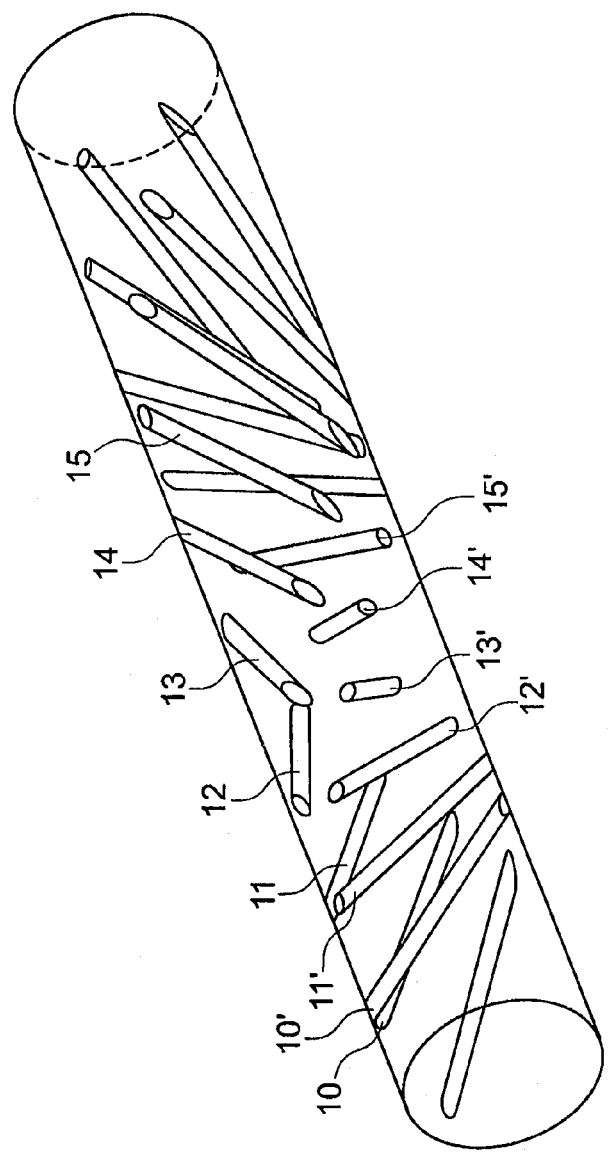
FIG. 6: The arrangement according to FIG. 5 in a diagrammatic perspective arrangement.

FIG. 6 shows in a diagrammatic representation a perspective view of the pump line 1 with sheath pipes 11 to 15 and 11' to 15' respectively arranged in it in the configuration corresponding to FIG. 5. The angle β of the sheath pipes 10, 11, 12, 13 amounts to 60° and that of the sheath pipes 10', 11', 12', 13' lying closer to the axis 3 amounts to 40°. The length of the sheath pipes available for the irradiation of the UV radiation into the medium is therefore about the same in each case.

Here, only a diagrammatic representation is provided to show that the sheath pipes of the radiators pass through the wall of the pump line 1 and are therefore accessible from the outside. The UV radiators themselves are then inserted into these sheath pipes, such that their radiating capacity can be given off to the pumped medium in the interior of the pump line 1.

In order to obtain a comparison between the performance capacity of the different in-line disinfection systems according to FIGS. 1-6, model calculations have been carried out according to what is referred to as the CFD method (Computational Fluid Dynamics). As simulation parameters, a throughflow volume of 2,300 m³/h was selected, a water transmission of 75%/1cm, radiator capacities of 120 W/cm=8, 400 W per radiator=750 W UV-C [biol. eff.] per radiator and a bacteria concentration of 1×10⁸ CFU/ml of *bacillus subtilis* (CFU=Colony Forming Units).

The following bacteria survival rates are derived:
FIG. 1: 4.7×10⁷ CFU/ml
FIG. 2: 6.3×10⁶ CFU/ml
FIG. 3: 1.7×10⁶ CFU/ml
FIG. 4: 5.6×10⁵ CFU/ml
FIGS. 5 and 6: 7.8×10² CFU/ml The calculations therefore produce a superior disinfection performance for the embodiment according to FIGS. 5 and 6, in which the radiators are arranged in two screw-shaped wound rows one behind another, wherein the two rows have a different distance interval r1 and r2 from the mid-axis of the pump line 1. The radiators are arranged in each case behind one another have an angle α of 30° to one another and the row of radiators arranged closer to the mid-axis is inclined at an angle β=40° against the radial direction while the row of radiators arranged further away from the mid-axis is inclined at an angle β=60° against the radial direction.

While in the description given above the structure has been explained on the basis of a straight cylindrical pipe for the pump line 1, the pump line can also be wound, angled or provided with another cross-section. The arrangement of the radiators in the pump line is then to be adapted accordingly.

Instead of the uniformly coiled embodiment described with parallel pairs of radiators, the radiators can also be aligned differently. For example, a displacement of the pairs of radiators in relation to one another in the direction of flow is also possible. In the direction of flow, the pairs of radiators in one plane can have a non-parallel relationship and these same pairs of radiators can have different angles β.

The invention claimed is:

1. Device for the sterilization of fluid media by means of UV radiation, comprising a pump line having a mid-axis, a radial plane perpendicular to the mid-axis, and a sidewall, by means of which the fluid media can be taken up and discharged along a plurality of possible flow paths collectively having a flow direction, wherein the sidewall is passed through by a number of UV-transparent sheath pipes in which UV radiators are arranged for the emission of UV radiation into the pump line, said sheath pipes comprising at least a first group of sheaths and a second group of sheaths, each group comprising a series of sheaths helically arranged one behind another in the flow direction of the pump line, with each adjacent sheath in the series circumferentially offset by an angle α in relation to one another, the first group of sheaths having midpoints that pass through a first helical path winding about the mid-axis of the pump line, each sheath of the first group disposed at a first non-zero angle $β_1$ relative to the radial plane, and the second group of sheaths having midpoints that pass through a second helical path, which differs from the first helical path, and each sheath of the second group disposed at a second non-zero angle $β_2$ relative to the radial plane different than the first angle $β_1$.

2. Device according to claim 1, wherein the angle α amounts to between 15° and 45°.

3. Device according to claim 1, wherein the angle α is about 30°.

4. Device according to claim 1, wherein the sheath pipes are inclined against the radial plane of the pump line by an angle β of 30° to 70°.

5. Device according to claim 1, wherein one sheath pipe of one of the groups of sheath pipes is arranged in relation to a mid-axis of the pump line next to a sheath pipe of the other group of sheath pipes and wherein the groups in each case form a screw-shaped row.

6. Device according to claim 5, wherein the groups have different distance intervals from the mid-axis, namely a first group having a large average distance interval, and a second group having a small average distance interval.

7. Device according to claim 6, wherein the first group is aligned at a large angle $β_1$ of 50° to 70° to the radial plane and the second group is aligned at a smaller angle $β_2$ of 30° to 49° to the radial plane.

8. Device according to claim 1, wherein at least two groups of sheath pipes are provided, such that a first group has a larger average distance interval from a mid-axis of the pump line that is more than 50% of the radius of the pump line and a second group has a smaller average distance interval from the mid-axis that is less than 50% of the radius of the pump line.

9. Device according to claim 8, wherein the larger average distance interval amounts to 75% of the radius of the pump line and the smaller average distance interval is less than 20% of the radius of the pump line.

10. Device according to claim 8, wherein the axial distance interval is varied relative to the average distance interval within a group by +/−10% of the radius of the pump line.

11. Device according to claim 5, wherein each of the groups of sheath pipes comprises a total of 12 sheath pipes.

12. Device according to claim 5, wherein the first group of sheaths is interlaced with the second group of sheaths such that one sheath of the first group of sheaths is positioned longitudinally between sheaths of the second group of sheaths, and one sheath of the second group of sheaths is positioned longitudinally between sheaths of the first group of sheaths.

13. The device of claim 1, wherein each sheath pipe penetrates the sidewall in a first location and a second location, thereby defining a chord length projected on a plane perpendicular to the longitudinal axis, the sheath pipes in the first group having a different non-zero chord length from the sheath pipes in the second group, and the angles $\beta 1$ and $\beta 2$ compensating for the difference in chord length such that the sheath pipes in the first and second groups have approximately a same respective length exposed to the fluid media.

14. The device of claim 1, wherein the sheath pipes are arranged such that every possible flow path impinges on a sheath pipe containing a UV radiator at least once in the course of the pump line.

* * * * *